US011238961B2

(12) United States Patent
Hao et al.

(10) Patent No.: US 11,238,961 B2
(45) Date of Patent: *Feb. 1, 2022

(54) AUTOMATIC KNOWLEDGE-BASED FEATURE EXTRACTION FROM ELECTRONIC MEDICAL RECORDS

(71) Applicant: International Business Machines Corporation, Armonk, NY (US)

(72) Inventors: Bi Bo Hao, Beijing (CN); Gang Hu, Beijing (CN); Jing Li, Beijing (CN); Wen Sun, Beijing (CN); Guo Tong Xie, Beijing (CN); Yi Qin Yu, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 182 days.

This patent is subject to a terminal disclaimer.

(21) Appl. No.: 16/708,562

(22) Filed: Dec. 10, 2019

(65) Prior Publication Data

US 2020/0143919 A1   May 7, 2020

Related U.S. Application Data

(63) Continuation of application No. 15/373,551, filed on Dec. 9, 2016, now Pat. No. 10,566,081.

(51) Int. Cl.
*G06F 16/00* (2019.01)
*G16H 10/60* (2018.01)
(Continued)

(52) U.S. Cl.
CPC ........ *G16H 10/60* (2018.01); *G06F 16/9017* (2019.01); *G06F 16/9024* (2019.01);
(Continued)

(58) Field of Classification Search
CPC ........ G16H 10/60; G16H 50/30; G16H 50/70; H04L 67/2833; H04L 67/10; G06F 16/9017; G06F 16/9024; G06F 16/90335
See application file for complete search history.

(56) References Cited

U.S. PATENT DOCUMENTS 8,700,589 B2    4/2014  Tymoshenko et al.
2004/0243552 A1  2/2004  Titemore et al.
(Continued)

FOREIGN PATENT DOCUMENTS

CN    105447609        3/2016
JP    2006313501 A    9/2010
(Continued)

OTHER PUBLICATIONS

Notice of Reasons for Refusal for Japanese Patent Application No. 2019-530142 dated Jan. 14, 2021.
(Continued)

*Primary Examiner* — Alexander Khong
(74) *Attorney, Agent, or Firm* — Fleit Intellectual Property Law; Thomas S. Grzesik (57) ABSTRACT

A method, device, and computer program storage product for generating a query to extract clinical features into a set of electronic medical record (EMR) tables based on clinical knowledge. A knowledge tree is constructed according to a set of clinical knowledge data. An EMR graph corresponding to a set of EMR tables is obtained. The EMR graph comprises at set of table nodes and a set of attribute nodes. The set of table nodes and the set of attribute nodes represent a structure of each EMR table in the set of EMR tables and a reference relationship among attributes of set of EMR tables. A plurality of sub-queries is generated based on the
(Continued)

knowledge tree and the EMR graph. At least one query is generated by combining the plurality of sub-queries according to the knowledge tree.

25 Claims, 6 Drawing Sheets

(51) Int. Cl.
  *G06F 16/901* (2019.01)
  *G06F 16/903* (2019.01)
  *H04L 29/08* (2006.01)
  *G16H 50/30* (2018.01)
  *G16H 50/70* (2018.01)

(52) U.S. Cl.
  CPC ....... *G06F 16/90335* (2019.01); *G16H 50/30* (2018.01); *G16H 50/70* (2018.01); *H04L 67/10* (2013.01); *H04L 67/2833* (2013.01)

(56) References Cited

U.S. PATENT DOCUMENTS

| | | | |
|---|---|---|---|
| 2004/0078236 A1 | 4/2004 | Stoodley et al. | |
| 2011/0040713 A1* | 2/2011 | Colman | A61B 5/7264 706/16 |
| 2011/0047169 A1* | 2/2011 | Leighton | G16H 50/70 707/756 |
| 2011/0113069 A1* | 5/2011 | Morgan | G06F 40/289 707/794 |
| 2014/0039931 A1 | 2/2014 | Joe et al. | |
| 2014/0059084 A1* | 2/2014 | Adams | G06F 16/9024 707/798 |
| 2015/0127379 A1 | 5/2015 | Sorenson | |
| 2015/0286788 A1 | 10/2015 | Arkoff | |
| 2016/0019299 A1 | 1/2016 | Boloor et al. | |
| 2016/0019365 A1 | 1/2016 | Ober, Jr. | |
| 2016/0063195 A1 | 3/2016 | Li et al. | |
| 2016/0306791 A1 | 10/2016 | Allen et al. | |
| 2017/0169169 A1* | 6/2017 | Kido | G06F 16/2457 |

FOREIGN PATENT DOCUMENTS

| | | |
|---|---|---|
| JP | 2015170214 A | 9/2015 |
| WO | 2015081086 | 6/2015 |

OTHER PUBLICATIONS

Yesha, R., et al., "A Graph-Based Method for Analyzing Electronic Medical Records", IEEE/ACM International Conference on Advances in Social Networks Analysis and Mining, Aug. 25-28, 2015, pp. 1-6. Aug. 25, 2015.

Kim, J., et al., "Extracting Clinical Relations in Electronic Health Records Using Enriched Parse Trees", Procedia Computer Science, Dec. 2015, pp. 1-10, vol. 53. Dec. 2015.

Yuwen, S., et al., "Standardizing the Medical Data in China", Journal of Convergence Information Technology, Aug. 2011, pp. 1-10, vol. 6, No. 8. Aug. 2011.

Examination Report Under Section 18(3) for Application No. GB1907907.8 dated Jul. 24, 2019.

International Search Report and the Written Opinion of the International Searching Authority for International Application No. PCT/CN2017/109286 dated Nov. 3, 2017.

Non-Final Office Action received for U.S. Appl. No. 15/373,551 dated Apr. 25, 2019.

List of IBM Patents or Patent Applications Treated as Related.

* cited by examiner

T1: Patient

| PID+ | gender | age | ... |
|---|---|---|---|
| P1 | M | 67 | ... |
| ... | ... | ... | ... |

T2: Encounter

| EID+ | diag | dept | PID* | ... |
|---|---|---|---|---|
| E1 | DM | D1 | P1 | ... |
| ... | ... | ... | ... | ... |

T3: Lab Test

| LID+ | EID* | date | tech | ... |
|---|---|---|---|---|
| L1 | E1 | 15-10-11 | Tech1 | ... |
| ... | ... | ... | ... | ... |

T4: Lab Test Index

| LName | LValue | LID* | ... |
|---|---|---|---|
| HbA1C | 10.5 | L1 | ... |
| ... | ... | ... | ... |

AUTOMATIC KNOWLEDGE-BASED FEATURE EXTRACTION FROM ELECTRONIC MEDICAL RECORDS

BACKGROUND

The present disclosure generally relates to the field of databases, and more specifically, to a method, system and a computer program product for generating query messages to query electronic medical records to extract clinical features.

Nowadays, the amount of clinical information in electronic medical record (EMR) systems is rapidly increasing. Clinical information is typically stored in form of relational datasets. Different hospitals or medical institutions may store EMR data into EMR datasets or EMR tables using different schemas. There are universal requirements of feature extraction/derivation from EMR data. Descriptive and predictive analysis on clinical datasets, feature extraction, and feature construction is typically labor-intensive. Therefore, health professionals are generally unable to efficiently extract or evaluate clinical knowledge using the EMR data. Schemas of EMR datasets for different sources vary and have to be changed into a unified schema so that query messages may be generated for querying EMR datasets to obtain information in a retrieval system. This is a labor-intensive process and is not robust. It would be desirable to integrate these EMR datasets of different schemas and use them to retrieve clinical features. It would be desirable to integrate these EMR datasets of different schemas and use them to retrieve clinical features.

SUMMARY

To address the issue of difference in schemas of EMR datasets, one or more embodiments propose a technique for automatically extracting clinical knowledge and/or evaluating clinical rules from EMR datasets in arbitrary relational schema. One or more embodiments propose a method, system and computer program product for generating queries for extracting clinical features from EMR datasets.

In one embodiment, a method for generating a query to extract clinical features into a set of electronic medical record (EMR) tables based on clinical knowledge is provided. The method comprises obtaining a knowledge tree is constructed according to a set of clinical knowledge data. An EMR graph corresponding to a set of EMR tables is obtained. The EMR graph comprises at set of table nodes and a set of attribute nodes. The set of table nodes and the set of attribute nodes represent a structure of each EMR table in the set of EMR tables and a reference relationship among attributes of set of EMR tables. A plurality of sub-queries is generated based on the knowledge tree and the EMR graph. At least one query is generated by combining the plurality of sub-queries according to the knowledge tree.

In another embodiment, a device for generating a query to extract clinical features into a set of electronic medical record (EMR) tables based on clinical knowledge is provided. The device comprises at least one processor and a memory operatively coupled to the at least one of the processor. A set of computer program instructions is stored in the memory and executed by the at least one in order to perform a plurality of actions. The plurality of actions comprises obtaining a knowledge tree is constructed according to a set of clinical knowledge data. An EMR graph corresponding to a set of EMR tables is obtained. The EMR graph comprises at set of table nodes and a set of attribute nodes. The set of table nodes and the set of attribute nodes represent a structure of each EMR table in the set of EMR tables and a reference relationship among attributes of set of EMR tables. A plurality of sub-queries is generated based on the knowledge tree and the EMR graph. At least one query is generated by combining the plurality of sub-queries according to the knowledge tree.

In a further embodiment, a computer program product for generating a query to extract clinical features into a set of electronic medical record (EMR) tables based on clinical knowledge is provided. The computer program product comprises a computer readable storage medium having program instructions embodied therewith. The program instructions are executable by at least one processor to cause the at least one processor to perform a method. The method comprises obtaining a knowledge tree is constructed according to a set of clinical knowledge data. An EMR graph corresponding to a set of EMR tables is obtained. The EMR graph comprises at set of table nodes and a set of attribute nodes. The set of table nodes and the set of attribute nodes represent a structure of each EMR table in the set of EMR tables and a reference relationship among attributes of set of EMR tables. A plurality of sub-queries is generated based on the knowledge tree and the EMR graph. At least one query is generated by combining the plurality of sub-queries according to the knowledge tree.

One or more embodiments provide a novel solution for automatic, knowledge-based feature extraction from EMR datasets in arbitrary relational schema. Compared with existing approaches in the field of clinical data analysis, embodiments may significantly reduce human efforts required on knowledge-based feature engineering, and thus are very useful for data mining in clinical knowledge in the literatures and the heterogeneous EMR datasets.

DETAILED DESCRIPTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

Figure 1:
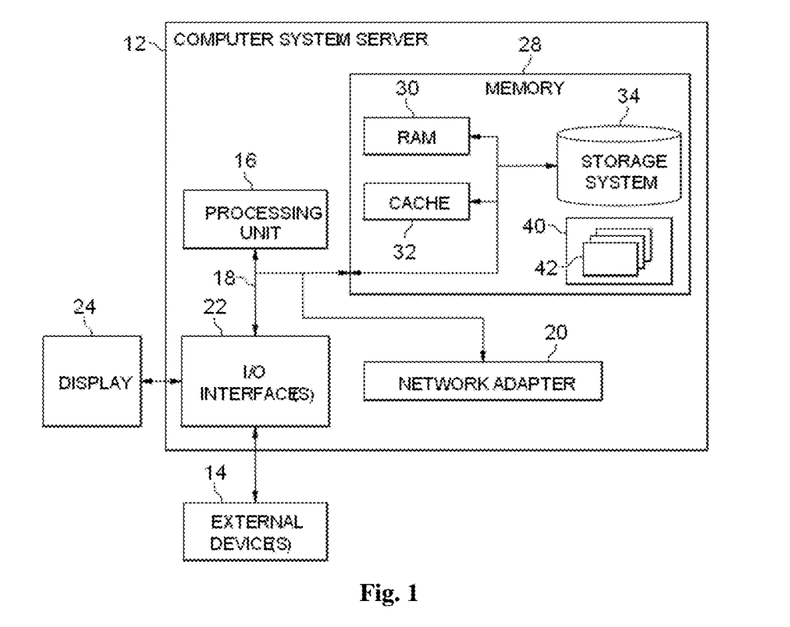
FIG. 1 shows an exemplary computer system according to one embodiment of the present disclosure.

Referring now to FIG. 1, one example of a computer system/server 12 applicable to one or more embodiments is shown. Computer system/server 12 is only illustrative and is not intended to suggest any limitation as to the scope of use or functionality of the various embodiments discussed herein. At least in some instances, one or more embodiments are implemented within the computer system/server 12. FIG. 1 shows the computer system/server 12 in the form of a general-purpose computing device. The components of computer system/server 12 may include, but are not limited to, one or more processors or processing units 16, a system memory 28, and a bus 18 that couples various system components including system memory 28 to processor 16. Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media. System memory 28 may include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 may be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media may be provided. In such instances, each may be connected to bus 18 by one or more data media interfaces. As will be further depicted and discussed below, memory 28 may include at least one program product having a set (e.g., at least one) of program modules that are configured to carry out the functions of one or more embodiments.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of one or more embodiments discussed herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication may occur via Input/Output (I/O) interfaces 22. Still yet, computer system/server 12 may communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components may be used in conjunction with computer system/server 12. Examples, include, but are not limited to: microcode, device drivers, redundant processing units, external disk drive arrays, RAID systems, tape drives, and data archival storage systems, etc.

To better understand various the various embodiments discussed herein, it would be advantageous to introduce some related knowledge, and provide an introduction of electronic medical records and clinical knowledge in the context of this disclosure. In one embodiment, queries are automatically composed into electronic medical records in an arbitrary formal schema based on clinical knowledge. The queries may then be used for extracting clinical features from the electronic medical records.

I. Electronic Medical Records

Figure 2:
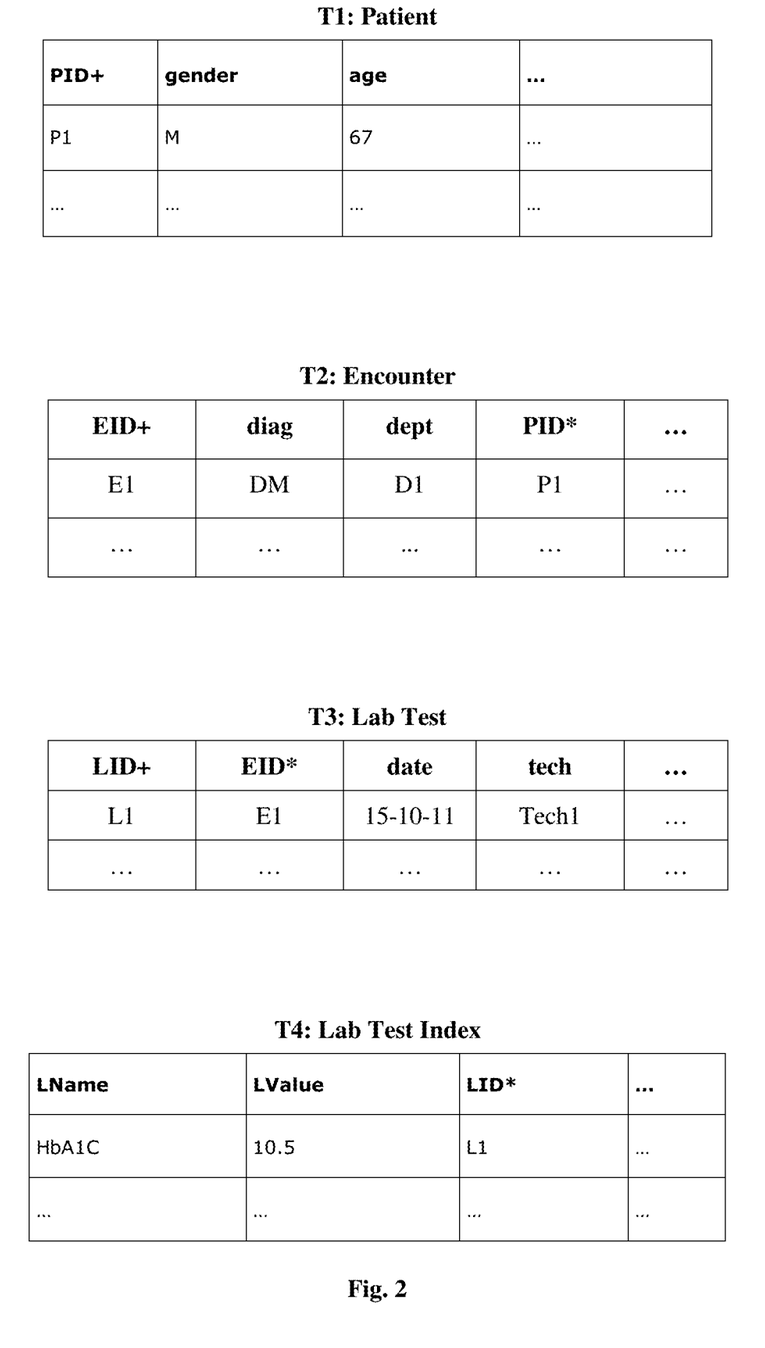
FIG. 2 illustratively shows an example of EMR dataset in table form according to one embodiment of the present disclosure.

An Electronic Medical Record (EMR) is a digital record of medical history and/or health information of patient and population. In one embodiment, electronic medical records (EMRs) are stored in formalized EMR datasets. The schema of an EMR dataset may vary depending on different database systems and/or different hospitals/medical institutions. FIG. 2 shows one example of an EMR dataset. The dataset includes formal tables. For simplicity, there are only four tables T1, T2, T3, and T4 illustrated in FIG. 2.

Table T1 is entitled Patient Table and includes basic data of patients. The first row of table T1 includes attributes (also referred to as "attribute names") and the second row and other rows (not shown) include values of the attributes (also referred to as "attribute values"). In table T1, attribute "PID" means patient identifier (ID) which uniquely identifies a patient. "PID" is affixed with a symbol "+" to indicate that "PID" serves as the primary key of table T1. Attribute "gender" means gender of patient. Attribute "age" means age of patient. The second row represents a data record for a patient. It comprises attribute values "P1", "M" and "67" respectively corresponding to the three attributes "PID", "gender", and "age". Value "P1" is the ID of a patient, "M" means the patient is male, and "67" is the patient's age. Table T1 may include basic data for different patients. FIG. 2 only illustratively shows three columns and two rows. In practical implementations, the number of columns and the number of rows are not thus limited.

Table T2 is called Encounter Table and stores data for hospital visits by patents. The first row of table T2 includes attributes and other rows include attribute values. There are shown four attributes in the first row. Attribute "EID" means encounter identifier (ID), which uniquely identifies a hospital visit by a patient. "EID" is affixed with a symbol "+" to indicate that "EID" serves as the primary key of table T2. Attribute "diag" means a diagnosis result of the hospital visit. Attribute "dept" means department of hospital. In addition, "PID" means the same as in T1, except that it is affixed with a symbol "*" to indicate that here it serves as a foreign key of T2. With the foreign key "PID", reference may be made to table T1. The second row represents a data record for a hospital visit by a patient. The attribute values "E1", "DM", "D1" and "P1" in the second row respectively corresponding to the four attributes "EID", "diag", "dept" and "PID". "E1" is an encounter ID, "P1" is a patient ID, "DM" is the diagnosis result of patient "P1", which is the abbreviation of "diabetes mellitus" and "D1" is the ID of clinical department visited by patient "P1". Table T2 may include information for different patients and may include multiple rows for different hospital visits by a particular patient. In FIG. 2, it only illustratively shows four columns and two rows. In practical implementations, the number of columns and the number of rows are not thus limited.

Table T3 is called Lab Test Table and stores data on laboratory tests made for patients in one or more hospital visits. The first row of table T3 includes attributes and other rows include values. There are shown four attributes in four columns of the first row. Attribute "LID" means lab test identifier (ID), which uniquely identifies a lab test. "LID" is affixed with a symbol "+" to indicate that "LID" serves as the primary key of T3. "EID" means the same as in table T2 and may serve as a foreign key of T3, as depicted by a symbol "*". Attribute "date" means date of lab test. Attribute "tech" means technician for lab test. The second row represent a data record for lab test, comprising values "L1", "E1", "15-10-11" and "Tech1" respectively corresponding to the four attributes "LID", "EID", "date" and "tech". "L1" is a lab test ID, "E1" is an encounter ID, "15-10-11" is the date of lab test "L1" and "Tech1" is the ID of the technician responsible for the lab test "L1". Table T3 may include information for different patients, and may include multiple rows for a particular patient who might take several lab tests during a single hospital visit. Again, there is no limit to the number of columns and rows that may be included in table T3.

Table T4 is called Lab Test Index Table and stores data on lab test indexes of lab tests. The first row of Table T4 includes attributes and other rows include attribute values. There are shown three attributes in three columns in the first row. Attribute "LName" means lab test index name, which uniquely identifies a lab test index. "LValue" means value of the lab test index. In addition, "LID" is the same as in table T3 and may serve as a foreign key of T4, as depicted by a symbol "*" affixed to it. The second row represents a data record for a lab test index. The values "HbA1C", "10.5", "L1" mean a lab test index named "HbA1C" is conducted in lab test L1 and the result value of lab test index "HbA1C" is "10.5". Table T4 may include information for different lab tests and for different patients, and may include multiple rows for a single lab test. Again, there is no limit to the number of columns and rows that may be included in table T4.

II. Clinical Knowledge

Clinical knowledge refers to the body of information about diseases, mechanisms and pathogenesis, therapies and interactions, and interpretation of lab tests, which is broadly applicable to decisions about multiple patients and public health policies. A body of clinical knowledge may be formalized into a set of clinical rules. An example of such a set of clinical rules is listed as the following.

R1: Blood glucose control satisfied: 80% of blood glucose value is satisfied (fasting blood glucose<7.5 mmol/L or 2 h blood glucose<10 mmol/L) in one month;
R2: Blood glucose continues high: 80% of blood glucose value is high (fasting blood glucose>=9 mmol/L or 2 h blood glucose>=13 mmol/L) in three months;
R3: low glucose: the latest blood glucose is low (blood glucose<3.9 mmol/L);
R4: high risk patient: age>65 and has diabetes and HbA1c>9.0 in last three months.

In one embodiment, clinical knowledge is formal clinical rules such as those shown above. There are existing techniques formalizing clinical knowledge into formal clinical rules. To avoid obscuring the description of the various embodiments, details about the generation of clinical rules will be omitted herein.

Given an EMR dataset, it would be desirable to extract clinical features from the EMR dataset based on known clinical knowledge. For example, it would be desirable to look for high risk patents from the tables as shown in FIG. 2 based on, for example, the clinical rule R4, which may be interpreted as:

"High risk patients are those who are over 65 years, are suffering diabetes, with test index "HbA1c" being greater than 9.0 in a lab test within three months".

Figure 3:
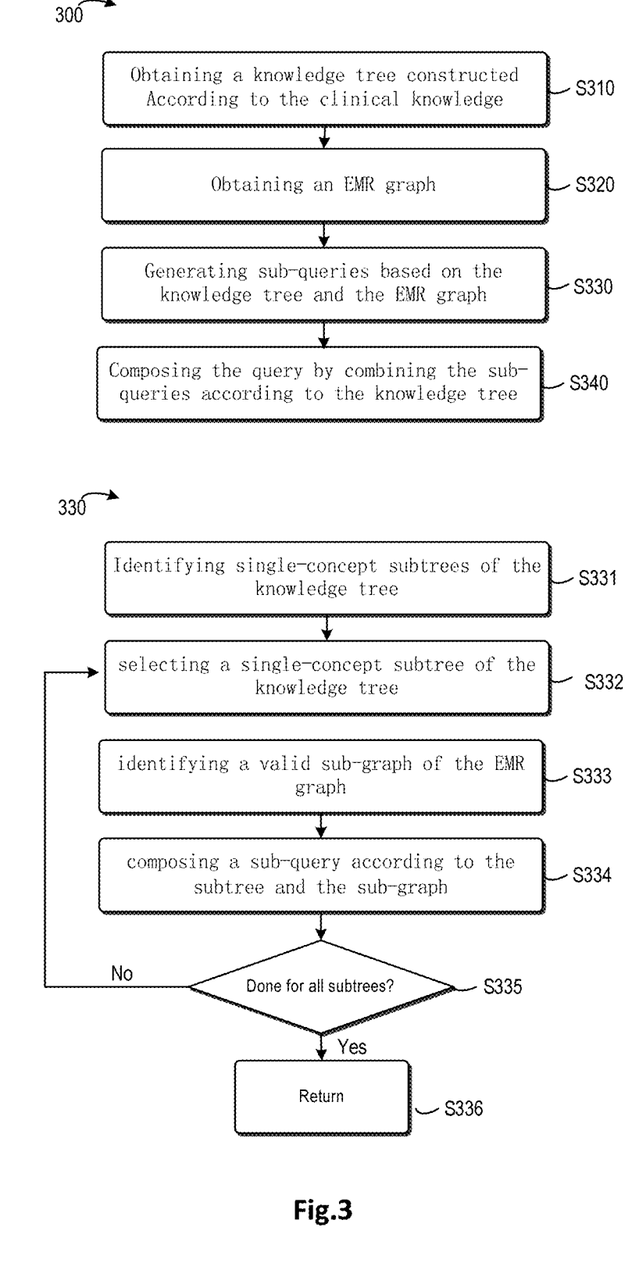
FIG. 3 is a flowchart illustrating a computer-implemented method for generating queries on EMR datasets according to one embodiment of the present disclosure.

A query is first composed to automatically extract the clinical feature. Now, with reference to FIG. 3, one or more embodiments for composing such a query are described. FIG. 3 is a flowchart illustrating a computer-implemented method 300 for generating a query for extracting clinical features into a set of EMR tables based on clinical knowledge according to one embodiment. Generally, method 300 comprises the following operations:

obtaining a knowledge tree constructed according to the clinical knowledge, as depicted by S310;
obtaining an EMR graph corresponding to the set of EMR tables, wherein the EMR graph is comprised of table nodes and attribute nodes to represent the structure of each of the EMR tables and the reference relationship among attributes of the EMR tables, as depicted by S320;
generating sub-queries based on the knowledge tree and the EMR graph, as depicted by S330; and
composing the query by combining the sub-queries according to the knowledge tree, as depicted by S340.

Figure 4A:
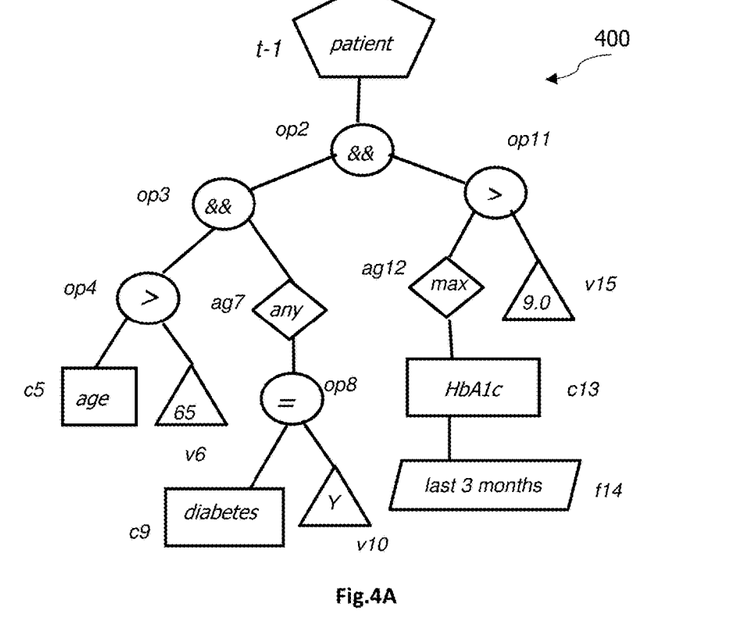
FIG. 4A illustratively shows a knowledge tree according to one embodiment of the present disclosure.

The above operations will now be discussed in detail. FIG. 4A illustratively shows a knowledge tree 400 according to one embodiment. A knowledge tree, in one embodiment, is used to express a body of knowledge and/or rules in tree structure. Assume method 300 is directed to clinical knowledge of clinical rule R4. According to clinical rule R4, if a patient is aged over 65 years, suffers from diabetes and his index of "HbA1c" is great than 9.0 in a lab test within last three months, then the patient is classified into the category of "high risk patients". Therefore, step S310 of obtaining a knowledge tree constructed according to the clinical knowledge obtains a knowledge tree 400 as shown FIG. 4A, which corresponds to rule R4.

As shown in FIG. 4A, knowledge tree 400 is comprised of nodes in different shapes. A pentagon node represents a target node, such as node t-1. An oval node represents an arithmetic/logical operator, such as operator nodes op2, op3, op4, op8, and op11. A rectangular node represents a clinical concept, such as concept nodes c5, c9, and c13. A diamond node represents an aggregation operator, such as aggregation nodes ag7 and Ag 12. A parallelogram node represents a concept filter, such as filter node f14. Finally, a triangular node represents a constant value, such as value nodes v6, v10, and v15.

As shown in FIG. 4A, target node t-1 is the root of knowledge tree 400. In one embodiment, the target node represents the target of clinical feature extraction. In this example, the target node is "patient". Generally, the target node may be regarded as the subject of the rule or knowledge tree. For instance, "patient" is the target of the rule "patients with condition of ABC is a high-risk patient", and the feature to be constructed would be a Boolean-typed one like "whether the patient is high risk" for each "patient". "Encounter" is the target of the rule "Encounters with condition of XYZ are outpatient follow-up encounters", and the feature to be constructed would be a Boolean-typed one "whether the encounter is an outpatient follow-up encounter" for each "encounter".

Operator nodes op2 and op3 represent a logical operator of "&&", or "AND". Operator nodes op4 and op11 represent a logical operator of ">", or "greater than". Operator node op8 represents a logical operator of "=", or "equal to". Concept nodes c5, c9, and c13 respectively represent clinical concepts "age", "diabetes", and "HbA1c". Aggregation nodes ag7 and ag12 respectively represent aggregation operator "any" and aggregation operator "max". Value node v10 represents a constant value of "Y", meaning "yes" or logical "true" in this example. Value node v15 represent a constant value of "9.0", which is a measuring value for the test index "HbA1c" in this example.

As will be appreciated by those skilled in the art, an aggregation operator is used to perform an operation on a collection of elements of same nature. In addition to "max" and "any", as mentioned above, another example of aggregation operator is "average", which is used to calculate an average of a collection of digital elements. Generally, an aggregation node indicates how to process the one-to-many or many-to-many relations in the feature construction. For example, when the target is the "patient" and the feature "whether the patient has ever lived in Beijing" is to be constructed. For each encounter, there might be a patient address record. Thus this one-to-many relation is to be processed by using the aggregation operator "any". Similarly, if the feature changes to "the patient's maximum body weight in the past", a "max" aggregation operator has to be applied to multiple weight measurement records. Typically, the aggregation operators are applied when the "target" is not the unique key in the relational table, or the table with the "target" attribute will join with another table with a one-to-many or many-to-many relation.

Filter node f14 represents a concept filter "last 3 months". As used herein, a filter node represents additional conditions that have to be met for an associated attribute of its parent node. In this example, filter node f14 representing "last 3 months" specifies the limitation that its parent node c13 requires some associated attribute of date type, and the attribute value should be in last three months.

Those familiar with knowledge expression tree shall understand that knowledge tree 400 includes three conditions, "age>65" (represented by nodes c5, op4 v6), "has diabetes" (represented by nodes c9, ag7, op8, v10) and "HbA1c>9.0 in last three months" (represented by nodes c13, op11, ag 12, v15, f14", combined by other nodes (op2 and op3). It should be noted that the use of different shapes is to visually differentiate different types of nodes. Those skilled in the art will appreciate that there might be other similar or equivalent ways of representing different types of nodes.

There are existing techniques that may construct knowledge trees to represent domain knowledge in various fields. Based on the above description, those skilled in the art will readily know how to construct a knowledge tree according to clinical knowledge in a variety of ways. One or more embodiments may use the techniques for the construction of knowledge tree to represent clinical knowledge, to implement step S310, namely, obtaining a knowledge tree constructed according to the clinical knowledge.

Return to FIG. 3. Having described step S310, now step 320 of method 300 will be described. Step S320 comprises obtaining an EMR graph corresponding to the set of EMR tables, wherein the EMR graph is comprised of table nodes and attribute nodes to represent the structure of each of the EMR tables and the reference relationship among attributes of the EMR tables. According to one embodiment, step S320 of obtaining an EMR graph corresponding to the set of EMR tables comprises converting the set of EMR tables to its equivalent graph representation.

Figure 5:
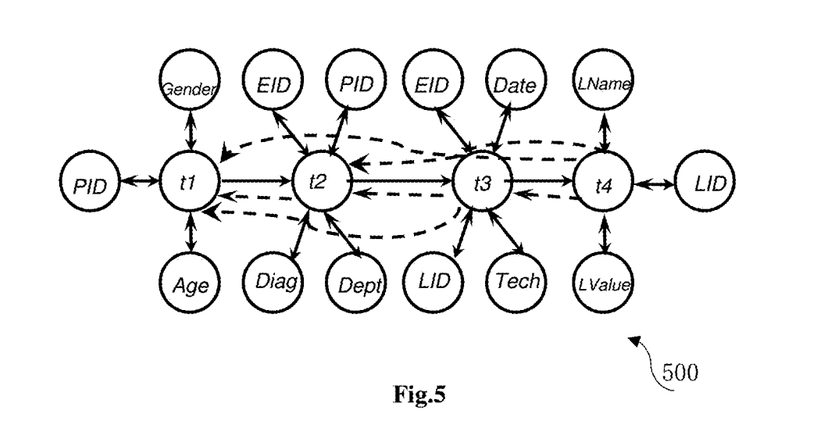
FIG. 5 illustratively shows an EMR graph converted from the EMR dataset of FIG. 2 according to one embodiment of the present disclosure.

FIG. 5 illustratively shows an EMR graph 500 converted from the set of EMR tables of FIG. 2, according to one embodiment. EMR graph 500 includes four table nodes t1, t2, t3, and t4 as well as attribute nodes bi-directionally connected to their associated table nodes. The graph 500 represents the structure of each of the EMR tables and the reference relationship among attributes of the four relational tables T1, T2, T3, and T4 in FIG. 2.

As shown in EMR graph 500, table node t1 stands for the primary key of table T1, i.e., the patient ID attribute "PID". Therefore, table node is also referred to as "key node". Table node t1 is bi-directionally connected to three attribute nodes "PID", "Gender", and "Age" via two plain edges. The three attribute nodes are corresponding to the three attributes "PID", "gender", and "age" of table T1. Likewise, table node t2 stands for the primary key for Table T2, i.e., "EID". Table node t2 is bi-directionally connected to four attribute nodes "EID", "Diag", "Dept", and "PID" via two plain edges, depicted by a bi-directional solid line in FIG. 5. The four attribute nodes are corresponding to the four attributes "EID", "diag", "dept", and "PID" of table T2. Table node t3 stands for the primary key for Table T3, i.e., "LID". Table node t3 is bi-directionally connected to four attribute nodes "LID", "EID", "Date", and "Tech" via two plain edges. The four attribute nodes are corresponding to the four attributes "LID", "EID", "date", and "tech" of table T3. Table node t4 stands for the primary key for Table T4, i.e., "LName". Table node t4 is bi-directionally connected to two attribute nodes "LName" and "LValue" via two plain edges. The two attribute nodes are corresponding to the two attributes "LName" and "LValue" of table T4.

Table nodes t1, t2, t3 and t4 are connected in the according to the following principle. If there is a foreign key reference between table tA to table tB, there is a plain edge from table node tB to table node tA. There is also an aggregation edge, which is depicted by a dotted arrow line in EMR graph 500, from table node tA to table node tB. In one embodiment, an aggregation edge means that the incoming node and the outgoing node's tables have a one-to-many or many-to-many relation, so that an "aggregation node" is required if the outgoing node's attributes have to be used to in the feature construction (joined with the incoming node). An aggregation edge is transitive. In other words, if table node tY is not directly connected to a table node tX but is reachable to table node tX by traversal via aggregation edges, then there is an aggregation edge from table node tX to table node tY. For example, in FIG. 5, there is a foreign key "PID" reference between table T2 and table T. Therefore, there is a plain edge from table node t1 to table node t2 and an aggregation edge from table node t2 to table node t1.

Likewise, there is a foreign key "EID" reference between table T3 and table T2, so there is a plain edge from table node t2 to table node t3 and an aggregation edge from table node t3 to table node t2. There is also a foreign key "LID" reference between Table T4 and Table T3, so there is a plain edge from table node t3 to table node t4 and an aggregation edge from table node t4 to table node t3. In addition, because table node t3 is not directly connected to t1 but is reachable to t1 by traversal via two aggregation edges, there is an aggregation edge from table node t3 to t1. For the same reason, there is an aggregation edge from table node t4 to t2. Similarly, there is an aggregation edge from table node t4 to t1.

In the above paragraphs, the relationship of the EMR dataset was discussed as represented by tables T1 to T4 in FIG. 2 and EMR graph 500 in FIG. 5. Generally speaking, an EMR graph represents attribute relationship of a set of relational EMR tables. The EMR graph is comprised of table nodes and attribute nodes. The table nodes respectively correspond to the EMR tables. Each table node is bi-directionally connected with all attribute nodes that respectively correspond to attributes of the EMR table corresponding to the table node. Table nodes are connected with each other by plain edges and aggregation edges based on the reference relationship of corresponding EMR tables.

Those skilled in the art shall appreciate that by proper programming according to the relationship, the EMR dataset represented by tables T1 to T4 may automatically be converted to EMR graph 500. Further, an EMR dataset in arbitrary relational schema may automatically be converted to an EMR graph similar to that shown in FIG. 5. In this way, an EMR graph 500 corresponding to the set of EMR tables as shown in FIG. 2 may be obtained in step S320.

Returning to FIG. 3, after steps S310 and S320, the next step S330 is generating sub-queries based on the knowledge tree and the EMR graph. In this step, a sub-query is generated in correspondence with each of concept nodes of knowledge tree 400 from EMR graph 500. In one embodiment, step S330 of generating sub-queries based on the knowledge tree and the EMR graph comprises:

identifying single-concept subtrees of the knowledge tree, as depicted by S331;

for each single-concept subtree of the single-concept subtrees:

selecting a single-concept subtree of the knowledge tree as depicted by S332;

identifying a valid sub-graph of the EMR graph by mapping a target node and a concept node of the single-concept subtree respectively to a table node and at least one attribute node of the EMR graph, as depicted by S333; and composing a sub-query according to the single-concept subtree and the valid sub-graph, as depicted by S334.

In other words, step S330, in one embodiment, is be executed with a process comprising steps S331 to S336 as shown in FIG. 3. First, step S331 is executed to identify single-concept subtrees of the knowledge tree. In one embodiment, a single-concept subtree refers to a subtree of a knowledge tree. The single-concept subtree comprises all nodes in the path starting from a concept node to the target node, or root node. In addition, the single-concept subtree also comprises any branch of each of the nodes in the path that comprises no other concept node. In other words, a single-concept subtree meets the following criteria: (1) there is only one concept node in the single-concept subtree; (2) the single-concept subtree comprises all nodes in the path starting from the one concept node to the target node; and (3) the single-concept subtree comprises any child of the nodes in the path, as long as there is no concept node in the child.

Figure 4B:
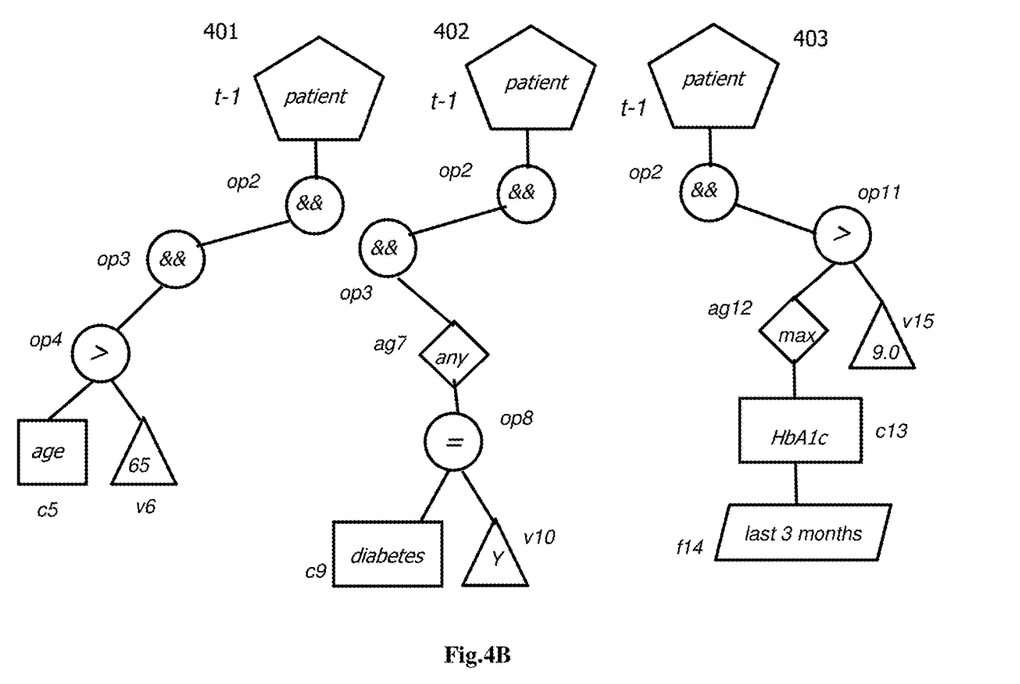
FIG. 4B illustratively shows a three single-concept sub-trees of the knowledge tree according to one embodiment of the present disclosure.

FIG. 4B shows three single-concept subtrees 401, 402 and 403 of knowledge tree 400. As shown in FIG. 4B, single-concept subtree 401 comprises nodes {t-1, op2, op3, op4, c5, v6}. Single-concept subtree 402 comprises nodes {t-1, op2, op3, ag7, op8, c9, v10}. Single-concept subtree 403 comprises nodes {t-1, op2, op11, ag12, c13, f14, v15}. In one embodiment, step S331 of identifying single-concept subtrees of the knowledge tree is performed by decomposing knowledge tree 400 in the following way. The path starting from the concept node c5 to the target node t-1 is found for each concept node c5. This path forms the backbone of one decomposed connected component (or subtree). For each node in this path, check all its children. If a child does not include any concept node, the child is added into the connected component (or subtree). When all the nodes in the path are checked, the subtree is one of the decomposed components of the entire knowledge tree. In this way, a single-concept subtree (also referred to "subtree" hereinafter) may be identified. It should be noted that for a knowledge tree with k concept nodes, k subtrees may be identified. For example, three subtrees 401, 402 and 403 may be identified for knowledge tree 400.

After step S331, step S332, S333, and S334 are executed iteratively for an individual subtree until all subtrees 401, 402 and 403 are processed. In step S332, subtree 401 is selected. Then, in step S333 a valid sub-graph of EMR graph 500 is identified. In one embodiment, this is performed by mapping the target node and the concept node of subtree 401 to a table node and at least one attribute node of EMR graph 500 (also referred to as "conceptual mapping" hereinafter).

In one embodiment, a valid sub-graph of the EMR graph is a sub-graph of the EMR graph that meets the following criteria: (1) there is a table node in the sub-graph matching with the target node; and (2) each attribute node in the sub-graph may reach the table node either directly or indirectly via a directed path. In one embodiment, conceptual mapping comprises any one of or any combination of the following: (1) mapping by attribute; (2) mapping by attribute value, and (3) mapping by applying additional filter. For the first type, the concept node is mapped to one or more attribute nodes that are matched with (same as or deemed to be same as) the concept of the concept node. For the second type, the concept node is mapped to some particular values of one or more attributes, and might be associated with additional attributes based on the concept data type and the mapped attributes' data type. For the third type, the concept node is mapped as the first or the second type mapping, but has additional associations with one or more attributes based on definition of the filter.

Figure 6A:
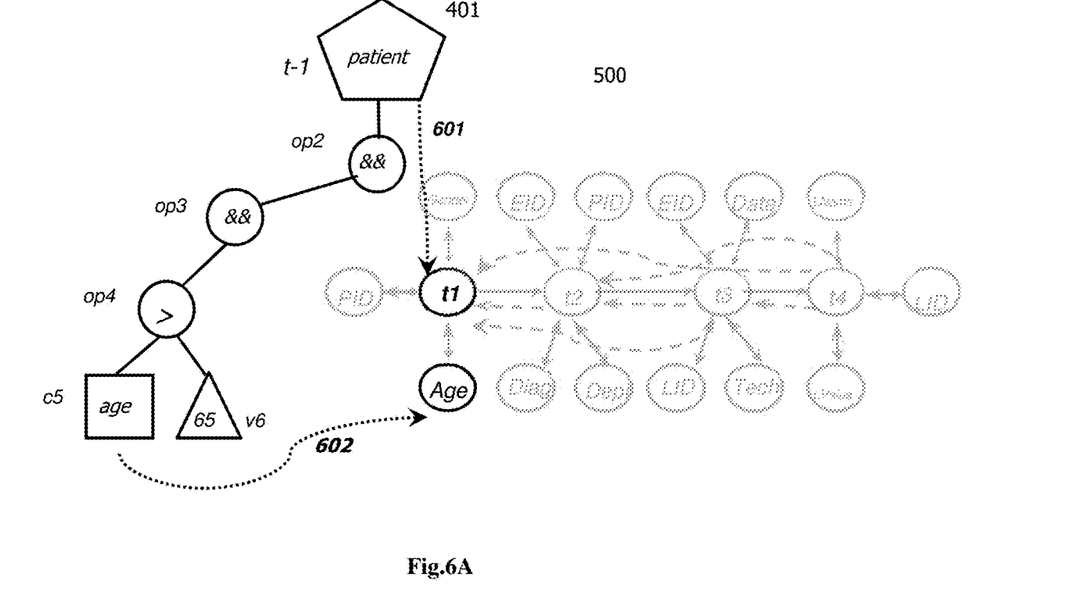
FIGS. 6A-6C illustratively show the process of generating sub-queries and composing a final query by mapping elements of the knowledge tree to elements of the EMR graph according to one embodiment of the present disclosure.

Referring to FIG. 6A, in step S333, conceptual mapping for subtree 401 is performed as follows. First, target node t-1 of subtree 401 is mapped to table node "t1" of EMR graph 500, as shown by arrow line 601. Then, concept node c5 is mapped to attribute node "Age" of EMR graph 500, as depicted by arrow line 602, since attribute "age" of table T1 is the same as the concept "age" for concept node c5 of subtree 401. As attribute node "Age" may directly reach table node "t1" matching with target node t-1, the sub-graph including attribute node "Age" and table node "t1" identified to be a valid sub-graph (also referred to "sub-graph" hereinafter). The valid sub-graph may be denoted as {t1, Age}, as highlighted in FIG. 6A In step S334, a sub-query is composed according to subtree 401 and valid sub-graph {t1, Age}. In this case, a sub-query may be composed based on the structure of subtree 401. Specifically, the structure of subtree 401 represents a condition of "age>65", so the sub-query is derived to be sub-query(1) as the following:

"t1.age>65" (1)

In one embodiment, a sub-query is derived according to the structure of subtree and the mapping of concept node to attribute node. First, the subject of the sub-query is generated. If the mapped attribute node (e.g., attribute node "Age" matching with concept node c5) is directly connected to the target node (e.g., target node t-1 mapped to table node t1) the attribute corresponding to the attribute node is the subject. In the above example, the subject is "age".

The process shown in FIG. 6A is an example of the first type of conceptual mapping. In the example, concept node c5 is mapped to one attribute node. However, a concept node might be mapped to more than one attribute node. If several attribute nodes may be mapped, each mapping is enumerated based on the matched score. For example, if the concept "age" may be mapped to attribute "Age", as well as "first pregnancy age", the mapping to the first attribute (with higher score) is evaluated first. The second one is evaluated if more query suggestions are needed.

In conceptual mapping, if an attribute node is connected to the target node by one or more plain edges crossing multiple table nodes, then one or more "joins" are applied to the involved table nodes based on the plain edges, and the mapped attribute in the joined table is the subject. If there are aggregation edges involved in the connected sub-graph, the corresponding aggregation operators are used in the table node joins.

After the process of generating sub-query is completed for subtree 401, it is determined whether the process is done for all of the subtrees, as depicted by block S335. If yes, the process of S330 is ended and control is returned, as depicted by block S336, so that step S340 is executed. Otherwise, the process proceeds to S332 to select another subtree, which is subtree 402 in this case.

Figure 6B:
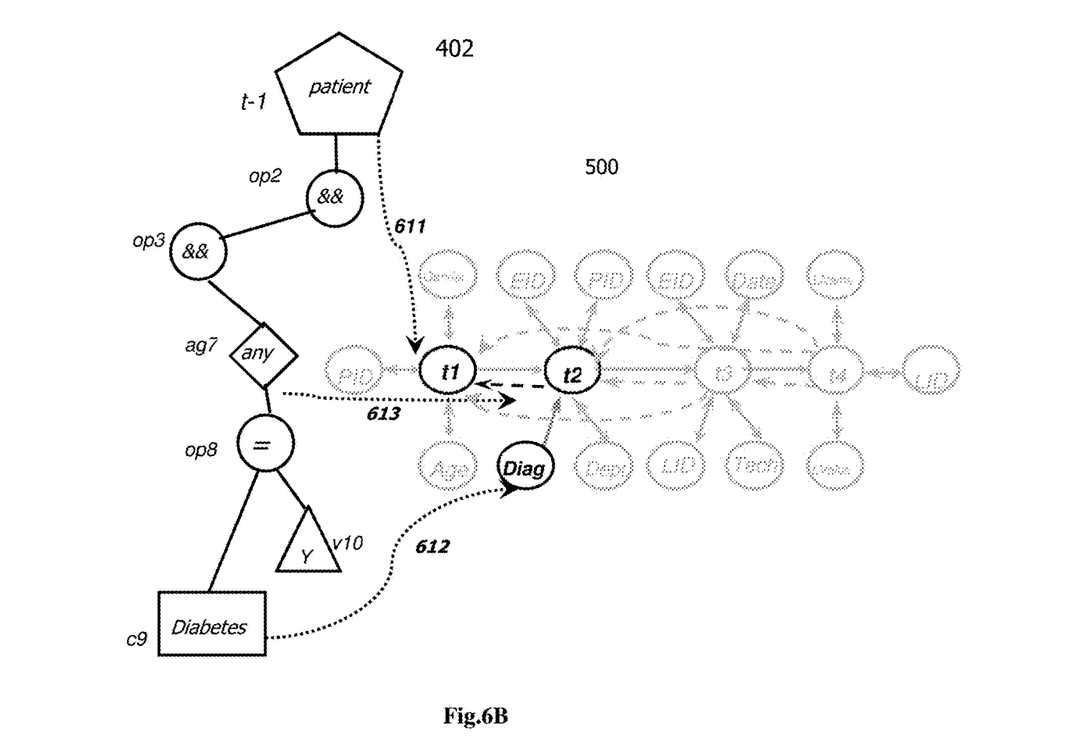

Refer to FIG. 6B. In step S333, target node t-1 of subtree 402 is mapped to table node "t1" of EMR graph 500, as depicted by arrow line 611. Then, because attribute value "DM" corresponding to attribute "diag" in table T2 is deemed to be the same as the concept "Diabetes" for concept node c9 of subtree 402 and attribute node "Diag" of EMR graph 500 corresponds to attribute "diag", concept node c9 is mapped to attribute node "Diag" as depicted by arrow line 612, which is connected to table node t2. At this point, the two mapped nodes, "Diag" and "t1", are not connected. However, there is an aggregation node ag7 in subtree 402, and it is applied to activate the aggregation edge <t2,t1> from table node "t2" to "t1", as depicted by arrow line 613, which means table "t2" may reach "t1" now. At this point, because attribute node "Diag" may reach table node "t1" indirectly via plain edge <Diag,t2> and the activated aggregation edge <t2,t1>, table node "t1" and table node "t2" and node "Diag" constitute a connected sub-graph of EMR 500, which may be identified to be a valid sub-graph {t1, t2, Diag}, as highlighted in FIG. 6B.

Then, in step S334, a sub-query is composed according to subtree 402 and sub-graph {t1, t2, Diag}. In particular, the structure of subtree 402 represents a condition of "any patient who has diabetes", so the sub-query is derived to be sub-query (2) as the following:

"t1 join t2 on PID, any(t2.diag='DM') group by
   PID"    (2)

The meaning of sub-query (2) may be interpreted as follows. Table T1 is joined with table T2 using attribute "PID" (thus each patient with unique ID will be a separate row of the new table), while generating a new (Boolean-typed) attribute if any diagnosis of one patient is equal to "DM" (diabetes mellitus).

In the conceptual mapping process described above, the aggregation node ag7 is used to connect mapped table nodes "t2" and "t1" by activating the aggregation edge <t2, t1>. For example, in the case that there are k aggregation nodes in the sub-tree, the k aggregation edges may be used to connect mapped nodes in EMR graph 500 to make them connected. The process shown in FIG. 6B is an example of the second type of conceptual mapping. With respect to the second type of conceptual mapping, the concept node of a subtree is mapped to some particular values of one or more attributes, and may be associated with additional attributes based on the concept data type and the mapped attributes' data type.

In the example of FIG. 6B, sub-graph {a, t2, Diag} constitutes a connected sub-graph and may be identified to be a valid sub-graph {t1, t2, Diag} as it meets the following criteria: (1) there is a table node in the sub-graph matching with the target node; and (2) each attribute node in the sub-graph may reach the table node either directly or indirectly via a directed path. In one embodiment, the term "connected sub-graph" is also used to denote valid sub-graph. Generally, if there is a directed path from a mapped node to the target node, the mapped node and the target node are connected, or the mapped node may reach the target node. If multiple nodes are mapped (i.e., one key node and one or more attribute nodes), the sub-graph is connected if (1) there is a directed path from the key node to the target node; and (2) for each attribute node there is a directed path from it to the key node. Here, the target node (e.g., t-1) is considered equivalent to the target node mapped node (e.g., t1).

Figure 6C:
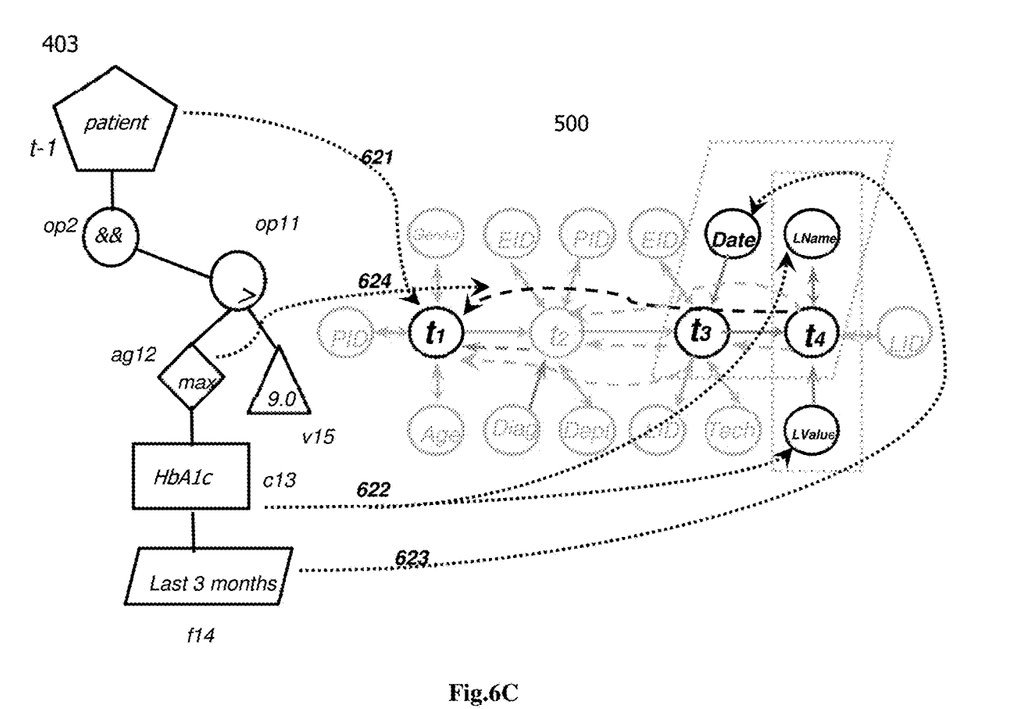

Referring to FIG. 6C, after sub-query (2) is generated subtree 403 is selected in step S332. Then, in step S333, the conceptual mapping for subtree 403 is performed as follows. First, the target node t-1 of subtree 403 is mapped to table node "t1" of EMR graph 500, as depicted by arrow line 621. Then, because the attribute value "HbA1c" corresponding to attribute "LName" of table T4 is the same as the concept "HbA1c" for concept node c13 of subtree 403, concept node c13 is mapped to node "LName" and node "LValue" of EMR graph 500, as depicted by a split arrow line 622. Further, because filter node f14 associated with concept node c13 defines a time-related condition, concept node c13 is mapped to attribute node "Date" of date type, as depicted by arrow line 623. Then, aggregation node ag12 in subtree 403 will be mapped to the aggregation edge from table node "t4" to table node "t1", as depicted by arrow line 624. Therefore, aggregation edge<t4, t1> is activated. At this point, attribute node "Date" may reach table node "t1" via plain edge <Date, t3>, plain edge<t3,t4> and aggregation edge <t4,t1>, "LName" may reach table node "t1" via a directed path "LName"→"t4"→"t1" and "LValue" may reach table node "t1" via a directed path "LValue"→"t4"→"t1". Therefore, conceptual mapping for subtree 403 results in the identification of a valid sub-graph {t1, t3, t4, Date, LName, LValue}, as highlighted in FIG. 6C.

In step S334, a sub-query is composed according to subtree 403 and sub-graph {t1, t3, t4, Date, LName, LValue}. In particular, according to the condition expressed by the structure of subtree 403, the sub-query is derived to be sub-query (3) as the following:

"t3 join t4 on LID, t4.LName=1-'HbA1c' and
   t3.Date>'2015-07-01' as t5; t1 join t5, max
   (t5.LValue)>9.0 group by PID    (3)

which queries all the patients whose recent maximum HbA1C testing result is larger than 9.0.

The process shown in FIG. 6C is an example of the third type of conceptual mapping. In one embodiment for the third type of conceptual mapping, the concept node is mapped as the first or the second type mapping, but has additional associations with one or more attributes based on the filter definition.

Referring back to FIG. 3, after step S334 is executed, the process proceeds to step S340. In step S340, the query is composed by combining the sub-queries (1), (2) and (3) according to knowledge tree 400. From operator "&&" for node op2 and operator "&&" for node op3 in knowledge tree 400, the query is the intersection of the three sub-queries, i.e., sub-query(1) && sub-query(2) && sub-query(3), or "t1.age>65" && "t1 join t2 on PID, any(t2.diag='DM') group by PID" && "t3 join t4 on LID, t4.LName='HbA1c' and t3.Date>'2015-07-01' as t5; t1 join t5, max(t5.LValue)>9.0 group by PID".

One or more embodiments also provide a corresponding device. In one embodiment, there is provided a device for generating a query for extracting clinical features into a set of EMR tables based on clinical knowledge. The device comprises one or more processors; a memory coupled to at least one of the processors; a set of computer program instructions stored in the memory. The set of computer program instructions are executed by at least one of the processors in order to perform actions of the follows: obtaining a knowledge tree constructed according to the clinical knowledge; obtaining an EMR graph corresponding to the set of EMR tables, wherein the EMR graph is comprised of table nodes and attribute nodes to represent the structure of each of the EMR tables and the reference relationship among attributes of the EMR tables; generating sub-queries based on the knowledge tree and the EMR graph; and composing the query by combining the sub-queries according to the knowledge tree.

According to one embodiment, the generation of sub-queries based on the knowledge tree and the EMR graph comprises:
identifying single-concept subtrees of the knowledge tree;
for each single-concept subtree of the single-concept subtrees:
selecting a single-concept subtree of the knowledge tree;
identifying a valid sub-graph of the EMR graph by mapping a target node and a concept node of the single-concept subtree respectively to a table node and at least one attribute node of the EMR graph; and
composing a sub-query according to the single-concept subtree and the valid sub-graph.

According to one embodiment, obtaining an EMR graph corresponding to the set of EMR tables comprises converting the set of EMR tables to its equivalent graph representation. The single-concept subtree of the knowledge tree, in one embodiment, is a subtree that comprises all nodes in the path starting from a concept node to the target node and any branch of each of the nodes that comprises no concept node.

According to one embodiment, the valid sub-graph of the EMR graph is a sub-graph of the EMR graph that meets the following criteria: (1) there is a table node in the sub-graph matching with the target node; and (2) each attribute node in the sub-graph may reach the table node either directly or indirectly via a directed path.

According to one embodiment, mapping the target node and the concept node of the single-concept subtree respectively to a table node and at least one attribute node of the EMR graph comprises any one of or any combination of the following: mapping by attribute; mapping by attribute value, and mapping by applying additional filter.

According to one embodiment, there is provided a computer program product for generating a query for extracting clinical features into a set of EMR tables based on clinical knowledge. The computer program product comprises a non-transitory computer readable storage medium. The program instructions are stored on the non-transitory computer readable storage medium. The program instructions are capable of being executed by at least one processor to cause the at least one processor to perform a method comprising:
obtaining a knowledge tree constructed according to the clinical knowledge;
obtaining an EMR graph corresponding to the set of EMR tables, wherein the EMR graph is comprised of table nodes and attribute nodes to represent the structure of each of the EMR tables and the reference relationship among attributes of the EMR tables;
generating sub-queries based on the knowledge tree and the EMR graph; and
composing the query by combining the sub-queries according to the knowledge tree.

According to one embodiment, generating sub-queries based on the knowledge tree and the EMR graph comprises:
identifying single-concept subtrees of the knowledge tree;
for each single-concept subtree of the single-concept subtrees:
selecting a single-concept subtree of the knowledge tree;
identifying a valid sub-graph of the EMR graph by mapping a target node and a concept node of the single-concept subtree respectively to a table node and at least one attribute node of the EMR graph; and
composing a sub-query according to the single-concept subtree and the valid sub-graph.

According to one embodiment, obtaining an EMR graph corresponding to the set of EMR tables comprises converting the set of EMR tables to its equivalent graph representation.

According to one embodiment, the single-concept subtree of the knowledge tree is a subtree that comprises all nodes in the path starting from a concept node to the target node and any branch of each of the nodes that comprises no concept node.

According to one embodiment, the valid sub-graph of the EMR graph is a sub-graph of the EMR graph that meets the following criteria: (1) there is a table node in the sub-graph matching with the target node; and (2) each attribute node in the sub-graph may reach the table node either directly or indirectly via a directed path.

According to one embodiment, the mapping the target node and the concept node of the single-concept subtree respectively to a table node and at least one attribute node of the EMR graph comprises any one of or any combination of the following: mapping by attribute; mapping by attribute value, and mapping by applying additional filter.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for generating a query to extract clinical features from a set of electronic medical record (EMR) tables based on clinical knowledge, the computer-implemented method comprising:
   determining at least one clinical feature to be extracted from a set of EMR tables;
   obtaining a knowledge tree for the at least one clinical feature, the knowledge tree being constructed according to a set of clinical knowledge data associated with the at least one clinical feature, wherein the knowledge tree represents one or more rules defining the at least one clinical feature;

obtaining, independent of the knowledge tree, an EMR graph corresponding to a set of EMR tables;

generating a plurality of sub-queries based on the knowledge tree and the EMR graph; and composing at least one query for extracting the at least one clinical feature from the set of EMR tables by combining the plurality of sub-queries according to the knowledge tree.

2. The method according to claim 1, wherein generating the plurality of sub-queries based on the knowledge tree and the EMR graph comprises:

identifying a plurality of single-concept subtrees of the knowledge tree; and for each single-concept subtree of the plurality of single-concept subtrees:

selecting a single-concept subtree of the knowledge tree identifying a valid sub-graph of the EMR graph by mapping a target node and a concept node of the single-concept subtree respectively to a table node and at least one attribute node of the EMR graph, and composing a sub-query according to the single-concept subtree and the valid sub-graph.

3. The method according to claim 2, where the single-concept subtree of the knowledge tree is a subtree that comprises all nodes in a path starting from a concept node to a target node and any branch of each of nodes that comprises no concept node.

4. The method according to claim 2, wherein the valid sub-graph of the EMR graph is a sub-graph of the EMR graph where there is a table node in the single-concept subtree matching a target node of the knowledge tree, and where there is a directed path from each attribute node in the single-concept subtree to the table node.

5. The method according to claim 2, wherein mapping the target node and the concept node of the single-concept subtree respectively to a table node and at least one attribute node of the EMR graph comprises at least one:

mapping by attribute;

mapping by attribute value; and mapping by applying at least one additional filter.

6. The method according to claim 1, wherein obtaining the EMR graph corresponding to the set of EMR tables comprises converting the set of EMR tables to an equivalent graph representation.

7. The method according to claim 1, further comprising:

extracting one or more clinical features from the set of EMR tables using the at least one query.

8. A device for generating a query to extract clinical features into a set of electronic medical record (EMR) tables based on clinical knowledge, the device comprising:

at least one processor;

a memory operatively coupled to the at least one processor; and a set of computer program instructions stored in the memory and executed by the at least one in order to perform actions of:

determining at least one clinical feature to be extracted from a set of EMR tables;

obtaining a knowledge tree for the at least one clinical feature, the knowledge tree being constructed according to a set of clinical knowledge data associated with the at least one clinical feature, wherein the knowledge tree represents one or more rules defining the at least one clinical feature;

obtaining, independent of the knowledge tree, an EMR graph corresponding to a set of EMR tables;

generating a plurality of sub-queries based on the knowledge tree and the EMR graph; and composing at least one query for extracting the at least one clinical feature from the set of EMR tables by combining the plurality of sub-queries according to the knowledge tree.

9. The device according to claim 8, wherein generating the plurality of sub-queries based on the knowledge tree and the EMR graph comprises:

identifying a plurality of single-concept subtrees of the knowledge tree; and for each single-concept subtree of the plurality of single-concept subtrees:

selecting a single-concept subtree of the knowledge tree, identifying a valid sub-graph of the EMR graph by mapping a target node and a concept node of the single-concept subtree respectively to a table node and at least one attribute node of the EMR graph, and composing a sub-query according to the single-concept subtree and the valid sub-graph.

10. The device according to claim 9, where the single-concept subtree of the knowledge tree is a subtree that comprises all nodes in a path starting from a concept node to a target node and any branch of each of nodes that comprises no concept node.

11. The device according to claim 9, wherein the valid sub-graph of the EMR graph is a sub-graph of the EMR graph where there is a table node in the single-concept subtree matching a target node of the knowledge tree, and where there is a directed path from each attribute node in the single-concept subtree to the table node.

12. The device according to claim 9, wherein mapping the target node and the concept node of the single-concept subtree respectively to a table node and at least one attribute node of the EMR graph comprises at least one:

mapping by attribute;

mapping by attribute value; and mapping by applying at least one additional filter.

13. The device according to claim 8, wherein obtaining the EMR graph corresponding to the set of EMR tables comprises converting the set of EMR tables to an equivalent graph representation.

14. The device according to claim 8, wherein the actions further comprise:

extracting one or more clinical features from the set of EMR tables using the at least one query.

15. A computer program product for generating a query to extract clinical features into a set of electronic medical record (EMR) tables based on clinical knowledge, the computer program product comprising a computer readable storage medium having program instructions embodied therewith, the program instructions executable by at least one processor, to cause the at least one processor to perform a method comprising:

determining at least one clinical feature to be extracted from a set of EMR tables;

obtaining a knowledge tree for the at least one clinical feature, the knowledge tree being constructed according to a set of clinical knowledge data associated with the at least one clinical feature, wherein the knowledge tree represents one or more rules defining the at least one clinical feature;

obtaining, independent of the knowledge tree, an EMR graph corresponding to a set of EMR tables, wherein the EMR graph comprises a set of table nodes and a set of attribute nodes, the set of table nodes and the set of attribute nodes representing a structure of each EMR table in the set of EMR tables and a reference relationship among attributes of set of EMR tables;

generating a plurality of sub-queries based on the knowledge tree and the EMR graph; and composing at least one query for extracting the at least one clinical feature from the set of EMR tables by combining the plurality of sub-queries according to the knowledge tree.

16. The computer program product according to claim 15, wherein generating the plurality of sub-queries based on the knowledge tree and the EMR graph comprises:

identifying a plurality of single-concept subtrees of the knowledge tree; and for each single-concept subtree of the plurality of single-concept subtrees:

selecting a single-concept subtree of the knowledge tree, identifying a valid sub-graph of the EMR graph by mapping a target node and a concept node of the single-concept subtree respectively to a table node and at least one attribute node of the EMR graph, and composing a sub-query according to the single-concept subtree and the valid sub-graph.

17. The computer program product according to claim 16, where the single-concept subtree of the knowledge tree is a subtree that comprises all nodes in a path starting from a concept node to a target node and any branch of each of nodes that comprises no concept node.

18. The computer program product according to claim 16, wherein the valid sub-graph of the EMR graph is a sub-graph of the EMR graph where there is a table node in the single-concept subtree matching a target node of the knowledge tree, and where there is a directed path from each attribute node in the single-concept subtree to the table node.

19. The computer program product according to claim 16, wherein mapping the target node and the concept node of the single-concept subtree respectively to a table node and at least one attribute node of the EMR graph comprises at least one:

mapping by attribute;

mapping by attribute value; and mapping by applying at least one additional filter.

20. The computer program product according to claim 15, wherein obtaining the EMR graph corresponding to the set of EMR tables comprises converting the set of EMR tables to an equivalent graph representation.

21. The computer program product according to claim 15, wherein the method further comprises:

extracting one or more clinical features from the set of EMR tables using the at least one query.

22. A computer-implemented method for generating a query to extract clinical features from a set of electronic medical record (EMR) tables based on clinical knowledge, the computer-implemented method comprising:

determining at least one clinical feature to be extracted from a set of EMR tables;

obtaining a knowledge tree for the at least one clinical feature, the knowledge tree being constructed according to a set of clinical knowledge data associated with the at least one clinical feature, wherein the knowledge tree represents one or more rules defining the at least one clinical feature;

obtaining, independent of the knowledge tree, an EMR graph corresponding to a set of EMR tables by converting the set of EMR tables to an equivalent graph representation;

generating a plurality of sub-queries based on the knowledge tree and the EMR graph based on identifying a plurality of single-concept subtrees of the knowledge tree;

composing at least one query for extracting the at least one clinical feature from the set of EMR tables by combining the plurality of sub-queries according to the knowledge tree; and searching for the at least one clinical feature within the set of EMR tables utilizing the at least one query.

23. The method according to claim 22, wherein generating the plurality of sub-queries based on the knowledge tree and the EMR graph further comprises:

for each single-concept subtree of the plurality of single-concept subtrees:

selecting a single-concept subtree of the knowledge tree, identifying a valid sub-graph of the EMR graph by mapping a target node and a concept node of the single-concept subtree respectively to a table node and at least one attribute node of the EMR graph, and composing a sub-query according to the single-concept subtree and the valid sub-graph.

24. A computer program product for generating a query to extract clinical features from a set of electronic medical record (EMR) tables based on clinical knowledge, the computer program product comprising a computer readable storage medium having program instructions embodied therewith, the program instructions executable by at least one processor, to cause the at least one processor to perform a method comprising:

determining at least one clinical feature to be extracted from a set of EMR tables;

obtaining a knowledge tree for the at least one clinical feature, the knowledge tree being constructed according to a set of clinical knowledge data associated with the at least one clinical feature, wherein the knowledge tree represents one or more rules defining the at least one clinical feature;

obtaining, independent of the knowledge tree, an EMR graph corresponding to a set of EMR tables by converting the set of EMR tables to an equivalent graph representation;

generating a plurality of sub-queries based on the knowledge tree and the EMR graph based on identifying a plurality of single-concept subtrees of the knowledge tree;

composing at least one query for extracting the at least one clinical feature from the set of EMR tables by combining the plurality of sub-queries according to the knowledge tree; and searching for the at least one clinical feature within the set of EMR tables utilizing the at least one query.

25. The computer program product according to claim 24, wherein generating the plurality of sub-queries based on the knowledge tree and the EMR graph further comprises:

for each single-concept subtree of the plurality of single-concept subtrees:

selecting a single-concept subtree of the knowledge tree, identifying a valid sub-graph of the EMR graph by mapping a target node and a concept node of the single-concept subtree respectively to a table node and at least one attribute node of the EMR graph, and composing a sub-query according to the single-concept subtree and the valid sub-graph.

* * * * *